United States Patent
Burnett et al.

(10) Patent No.: US 9,782,348 B2
(45) Date of Patent: *Oct. 10, 2017

(54) INGESTIBLE FORMULATIONS FOR TRANSIENT, NONINVASIVE REDUCTION OF GASTRIC VOLUME

(71) Applicant: BAROnova, Inc., San Carlos, CA (US)

(72) Inventors: Daniel R. Burnett, San Francisco, CA (US); Peter G. Edelman, Mukilteo, WA (US)

(73) Assignee: BAROnova, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/213,285

(22) Filed: Jul. 18, 2016

(65) Prior Publication Data

US 2016/0324774 A1    Nov. 10, 2016

Related U.S. Application Data (60) Continuation of application No. 14/178,568, filed on Feb. 12, 2014, now Pat. No. 9,421,246, which is a
(Continued)

(51) Int. Cl.
*A61K 9/00* (2006.01)
*A61K 9/20* (2006.01)
(Continued)

(52) U.S. Cl.
CPC ............ *A61K 9/0065* (2013.01); *A61F 5/003* (2013.01); *A61F 5/0036* (2013.01); *A61K 9/205* (2013.01); *A61K 9/2022* (2013.01); *A61K 9/2027* (2013.01); *A61K 9/2063* (2013.01); *A61K 9/2833* (2013.01); *A61K 9/4866* (2013.01);
(Continued)

(58) Field of Classification Search
CPC .. A61K 9/0065; A61K 9/2027; A61K 9/2022; A61K 9/205; A61K 9/2063; A61K 31/7088; A61K 38/38; A61K 31/765; A61K 31/78; A61K 38/16; A61K 31/715; A61K 9/4866; A61K 9/2833; A61K 2800/546; A61F 5/003; A61F 5/00; A61F 5/0036
See application file for complete search history.

(56) References Cited

U.S. PATENT DOCUMENTS 3,915,171 A    10/1975   Shermeta
4,315,509 A    2/1982   Smit
(Continued)

FOREIGN PATENT DOCUMENTS

DE    4012642    10/1991

*Primary Examiner* — Aradhana Sasan
(74) *Attorney, Agent, or Firm* — Levine Bagade Han LLP (57) ABSTRACT

Provided are ingestible polymeric formulations and oral dosage forms for the reduction of gastric volume in the treatment of overweight and obese patients. The formulation includes an acid-sensitive, gelatin coating over a dehydrated hydrophilic polymer. When ingested, the acid-sensitive coating is quickly dissolved by gastric secretions and the hydrophilic polymer is exposed to the aqueous environment of the gastric milieu. The polymer absorbs water and expands to the point that will not allow the polymer to pass beyond the pyloric valve, and the expanded polymer is therefore trapped in the stomach.

2 Claims, 5 Drawing Sheets

Related U.S. Application Data division of application No. 12/148,702, filed on Jan. 25, 2008, now Pat. No. 8,691,271, which is a continuation of application No. 10/741,177, filed on Dec. 19, 2003, now abandoned.

(60) Provisional application No. 60/468,131, filed on May 6, 2003, provisional application No. 60/434,367, filed on Dec. 19, 2002.

(51) Int. Cl.

| | | |
|---|---|---|
| *A61K 31/7088* | (2006.01) | |
| *A61K 38/38* | (2006.01) | |
| *A61K 31/765* | (2006.01) | |
| *A61K 31/78* | (2006.01) | |
| *A61K 38/16* | (2006.01) | |
| *A61K 31/715* | (2006.01) | |
| *A61K 9/48* | (2006.01) | |
| *A61K 9/28* | (2006.01) | |
| *A61F 5/00* | (2006.01) | |

(52) U.S. Cl.
CPC ........ *A61K 31/7088* (2013.01); *A61K 31/715* (2013.01); *A61K 31/765* (2013.01); *A61K 31/78* (2013.01); *A61K 38/16* (2013.01); *A61K 38/38* (2013.01); *A61K 2800/546* (2013.01)

(56) References Cited

U.S. PATENT DOCUMENTS

| | | |
|---|---|---|
| 4,432,968 A | 2/1984 | Page et al. |
| 4,485,805 A | 12/1984 | Foster, Jr. |
| 4,739,758 A | 4/1988 | Lai et al. |
| 4,878,905 A | 11/1989 | Blass |
| 4,899,747 A | 2/1990 | Garren et al. |
| 4,992,539 A | 2/1991 | Portney et al. |
| 5,007,790 A | 4/1991 | Shell |
| 5,234,454 A | 8/1993 | Bangs |
| 5,543,405 A | 8/1996 | Keown et al. |
| 5,750,585 A | 5/1998 | Park et al. |
| 5,945,457 A | 8/1999 | Plate et al. |
| 6,271,278 B1 | 8/2001 | Park et al. |
| 7,121,283 B2 | 10/2006 | Stack et al. |
| 9,421,246 B2 * | 8/2016 | Burnett .................. A61F 5/003 |
| 2002/0042473 A1 | 4/2002 | Trollsas et al. |
| 2002/0147208 A1 | 10/2002 | Fleshner-Barak et al. |
| 2003/0012734 A1 | 1/2003 | Pathak et al. |
| 2003/0021845 A1 | 1/2003 | Friedman et al. |
| 2003/0152622 A1 | 8/2003 | Louie-helm et al. |
| 2004/0234608 A1 | 11/2004 | Fleshner-barak et al. |

\* cited by examiner

INGESTIBLE FORMULATIONS FOR TRANSIENT, NONINVASIVE REDUCTION OF GASTRIC VOLUME

This application is a continuation of U.S. patent application Ser. No. 14/178,568 filed Feb. 12, 2014 (now U.S. Pat. No. 9,421,246 issued Aug. 23, 2016), which is a divisional of U.S. patent application Ser. No. 12/148,702 filed Jan. 25, 2008 (now U.S. Pat. No. 8,691,271 issued Apr. 8, 2014), which is a continuation of U.S. patent application Ser. No. 10/741,177 filed Dec. 19, 2003 (now abandoned), which claims the benefit of priority under 35 U.S.C., §119(e) of U.S. Provisional Patent Application No. 60/468,131 filed May 6, 2003, and U.S. Patent Application No. 60/434,367 filed Dec. 19, 2002, the entire contents of which are incorporated herein by reference.

FIELD OF THE INVENTION

The invention relates generally to polymeric formulations, especially polymers useful for weight loss methods and devices.

BACKGROUND OF THE INVENTION

Obesity is a condition of epidemic proportions in the United States. Recent government studies have indicated that up to 40% of Americans are obese, and of those, almost 20% are morbidly obese. In and of itself, however, obesity is not the problem. The difficulty with obesity arises with the multiple conditions, including cardiovascular disease, diabetes, and obstructive sleep apnea, that occur with this ubiquitous problem. There have been many attempts to treat obesity, most of which either have serious side effects or are ineffective.

For example, various diets, supplements, and pharmaceuticals have been developed in an attempt to treat obesity. Typically, these types of treatment have not provided any significant benefit. Indeed, some weight loss pharmaceuticals have been associated with many serious life-threatening conditions. To date, there are no commercially available supplements or drugs on the market that have been found to have significant success in weight reduction.

Recognizing this, the medical industry has turned to more extreme measures, the best example of which is the Roux-En-Y gastric bypass. More effective, but also potentially lethal, this major surgery with 1-2% mortality, 6 month recovery period and a price tag of tens of thousands of dollars, is still increasing in its popularity due to the inefficacy of other treatments. Gastric reduction, or simply removing a large segment of the stomach, is similar to gastric bypass in its potentially lethal combinations.

Progress was made, however, with the introduction of intragastric balloons, as described in U.S. Pat. Nos. 4,739,758; 5,234,454; 4,485,805; and 4,899,747. These balloons, designed to be placed surgically or endoscopically, are constructed of silicone and inflated once positioned in the stomach, thereby reducing effective gastric volume. These balloons were found to be effective in increasing the sensation of fullness in the patient and reducing weight by reducing intake.

Unfortunately, these intragastric balloons still required an invasive procedure and also generated ulcers and other complications due to having the inflexible silicone surface in contact with the stomach wall in the same orientation for months. Also, these devices require further invasive surgery or endoscopic procedures to reduce or increase the balloon volume in the common event that the balloon was filled too much or too little.

A further advancement was proposed by Ration in German Patent No. NDN-050003290517 in which a compressed cellulose derivative was utilized. This compressed cellulose derivative was coated with gelatin and was designed to be expanded once ingested into the stomach. The difficulty with this derivation is that cellulose is broken down at roughly equivalent rates in the stomach and small bowel. Thus, any partially digested masses of cellulose that have been passed from the stomach will remain intact in the intestine and cause a possible small bowel obstruction. This risk outweighs the possible benefit, in many cases making the therapy undesirable.

A similar difficulty is likely to be associated with the therapy described in U.S. Pat. Nos. 5,750,585 and 6,271,278. The polymers described therein do not exhibit differential degradation rates in the stomach and the intestine, thereby placing patients at risk for a small bowel obstruction. Therefore, there is a need in the industry to develop more methods and devices, especially noninvasive methods and devices useful for weight loss and/or weight management.

SUMMARY

The present invention is based, in pan, on the discovery that certain polymers can be modified so that they have a higher degradation rate in an intestine-like, environment than in a gastric-like environment, whose enzymatic and pH make up is different from each other. Accordingly the present invention provides polymeric formulations capable of being retained in a stomach for a certain period of time and being rapidly degraded upon entering into an intestine. The polymeric formulations provided, by the present invention can be used for various applications including delivery of therapeutics, e.g., in a stomach over a period of time, and reduction of gastric volume in the treatment of overweight and obese patients.

In one embodiment of the invention, there are provided oral dosage forms useful for gastric volume reduction. Such oral dosage forms, include, for example, a polymer that (i) swells upon absorbing water from gastric fluid to increase its size thereby promoting its gastric retention, (ii) maintains its physical integrity in a stomach for about 4 hours to 30 hours, and (iii) is degradable by an intestinal enzyme or exposure to an intestinal pH, e.g., 8.0, wherein the dosage form is in the form of a tablet or capsule that maintains the polymer in a packed mass prior to its ingestion and then rapidly disintegrates in the gastric fluid, to permit the polymer to disperse in the stomach and wherein the dosage form does not contain a drug.

In another embodiment, there are provided polymeric formulations including a hydrophilic polymer that (i) swells upon absorbing water from gastric fluid to increase its size thereby promoting its gastric retention, (ii) maintains its physical integrity in a stomach for at least 2 hours, e.g., from 2 to 30 hours, and (iii) degrades faster in an intestine than a stomach, wherein the polymer is cross linked through a linker which provides the polymer with a sensitivity towards an intestinal enzyme.

In still further embodiments, there are provided methods for reducing gastric volume in a subject. Such methods can be performed, for example, by administering to as subject in need thereof an oral dosage form described herein. In an alternative embodiment, such methods can be performed by administering to a subject in need thereof a polymeric formulation described herein.

In yet another embodiment, there are provided methods for delivering a drug. Such methods can be performed, for example, by administering to a subject in need of the drug a polymeric formulation described herein, wherein the formulation further contains the drug dispersed in the polymer.

DETAILED DESCRIPTION OF THE INVENTIONS

The present invention provides polymeric formulations capable of being retained in a gastric like environment for a certain period of time and being rapidly degraded upon entering into an intestine like environment. Specifically the present invention provides oral dosage forms and polymeric formulations useful for reduction of gastric volume in the stomach or delivering therapeutics to a subject, e.g., human.

The polymers utilized in the oral dosage forms and formulations of the invention are capable of being degraded differentially in an intestine like environment as compared to a gastric like environment. For example, the polymers of the present invention degrades faster in an environment with an enzymatic and/or pH make up characteristic of the intestine than that of the stomach. Usually such differential degradation is based on pH sensitivity of an entity or an entity's sensitivity to one or more intestinal specific substances, such as, bile, lipases, and other intestinal enzymes or entities and the like.

Sensitivity to intestinal enzymes or pH can be obtained by any suitable means available to one skilled in the art, e.g., chemical modification. For example, sensitivity to intestinal enzymes, e.g., lipases can be achieved through chemical modification of either natural entities, e.g., alginate, cellulose, and the like or modification of artificially synthesized entities, e.g., an acrylate. By acquiring one or more lipase-sensitive, fatty acid-like polymerizable groups and/or cross-linking groups, an entity can have optimal differential degradation characteristics in which degradation occurs much more rapidly in the intestine as compared to the gastric environment. Alternatively, differential degradation can be accomplished via incorporation of components that are selectively degraded in the intestine, e.g., fats, and need not be limited to proteins and polymers.

The oral dosage form or polymeric formulation of the present invention usually can include an acid-sensitive, gelatin coating over a dehydrated hydrophilic polymer. When ingested, the acid-sensitive coating is quickly dissolved by gastric, secretions and the hydrophilic polymer is exposed to the aqueous environment of the gastric milieu. The polymer absorbs water and expands to the point that will not allow the polymer to pass beyond the pyloric valve, and the expanded polymer is therefore trapped in the stomach. The expanded polymer remains in the stomach until acids and proteases or other enzymes in the stomach reduce its volume such that it is able to pass the pyloric valve into the intestine.

Although the polymeric formulation of the present invention is designed to be somewhat resistant to degradation by gastric secretions, it remains highly susceptible to the environment of the intestine, e.g., intestinal enzymes or pH. Thus, while the polymeric formulation of the present invention can remain in the stomach for many hours or even days, once it has passed into the intestine, it is rapidly degraded, thereby reducing the risk of small bowel obstruction. Since the polymer of the present invention degrades much more rapidly in an intestinal environment than in the stomach, the potential risk of small bowel obstruction is significantly reduced or virtually eliminated.

In addition, the formulations and dosage forms of the invention are designed to expand to a diameter that is sufficient to prevent passage beyond the pyloric valve, but will not cause small bowel obstruction or rupture, e.g., a diameter no greater than about 6 cm or so. Due to this size restriction, use of the present invention entails ingestion of multiple tablets until the subject begins to feel a sensation of fullness. The present invention avoids the complications of excessive gastric distension that is common after intragastric balloon placement. Once the oral dosage forms and polymeric formulations described herein pass beyond the pyloric valve and are degraded in the intestine, the subject simply ingests additional tablets.

According to one feature of the present invention, it provides oral dosage forms of polymers useful for gastric volume reduction. The oral dosage form of the present invention includes a polymer that (i) swells upon absorbing water from gastric fluid to increase its size thereby promoting its gastric retention, (ii) maintains its physical integrity in the stomach for a period of time and (iii) is degradable by an intestinal enzyme or exposure to an intestinal pH. The dosage form of the present invention can be in the form of a tablet or capsule, e.g., maintains the polymer in a packed mass prior to its ingestion and then rapidly disintegrates in the gastric fluid to permit the polymer to disperse in the stomach. In one embodiment, the dosage form of the present invention does not contain a drug. In another embodiment, the oral dosage form of the present invention maintains its physical integrity for at least 2 hours, 4 hours, or 6 hours. In yet another embodiment, the oral dosage form of the present invention maintains its physical integrity from about 4 hours to 30 hours, 6 hours to 24 hours, or 8 hours to 16 hours.

As used herein, the phrase "gastric volume reduction" means 1) any temporary reduction of available gastric volume, e.g., any temporary reduction of gastric, volume available to an ingested subject, 2) any temporary reduction of gastric capability with respect to content intake, or 3) any temporary sensation of gastric fulfillment or fullness.

As used herein, the phrase "physical integrity", when used with reference to the polymers described herein, means that the polymers do not significantly or appreciably dissolve, erode or otherwise decompose or degrade, e.g., the polymer chains remain substantially intact, and, if the polymers are cross-linked, that the cross-links remain substantially intact, thereby providing a three-dimensional polymeric network.

Polymers contemplated for use in the practice of the invention are typically water-soluble polymers or co-polymers, e.g., polymers or copolymers capable of swelling upon contacting with water. Such polymers include, for example, polyvinyl alcohol, poly(ethyloxazoline), poly(2-hydroxy ethylacrylate), poly 2-hydroxy ethylmethacrylate), polyacrylic acid, polysaccharides, proteins, polynucleic acids, and the like. In one embodiment, the polymers of the present invention is polyvinylacetate-polyvinylalcohol copolymers, poly(2-hydroxyethyl acrylate) and copolymers, poly and copolymers, or poly(2-hydroxyethylmethylacrylate) and copolymers.

As used herein, the term "polysaccharides" includes polysaccharides, polysaccharoses, sugars, and the like. Exemplary polysaccharides include starch, sodium starch glycolate, alginic acid, cellulose, carboxymethylcellulose, hydroxyethylcellulose, hydropropylcellulose, hydroxypropylmethylcellulose, ethylcellulose, carageenan, chitosan, chondroitin sulfate, heparin, hyaluronic acid, pectinic acid, chitosan, hyaluronic acid, xanthan gum, starch, maltodextrins, corn syrup, alginates, and the like. Proteins contemplated for use include, but are not limited to, water soluble proteins, e.g., albumin, gelatin, and the like.

According to one embodiment of the present invention, the oral dosage form or polymeric formulation of the present invention includes a polymer that is biocompatible and/or pH sensitive, e.g., sensitive to intestinal pH. Such oral dosage form or polymeric formulation typically includes a dehydrated combination of a biocompatible polymer, e.g., an alginate and a solubilizer/stabilization agent, e.g., xanthan gum, propylene glycol alginate, and the like (to allow for maintenance of a firm solid polymer within the gastric environment) covered with an acid-sensitive coating e.g., a gelatin). Alginate itself precipitates to a certain degree in the acidic environment of the stomach and so likely requires an additional component in order to prevent precipitation. In one embodiment, the additional component is propylene glycol alginate. In another embodiment, the solubilizer/stabilization agent is sensitive to intestinal pH. For example, propylene glycol alginate forms a solid in the stomach but becomes viscous at intestinal pH. Typically, about half of the polymer of alginate with propylene glycol alginate is degraded after 3 to 4 hours at intestinal pH.

According to another embodiment of the present invention, the polymers described herein are cross-linked. Cross-linking can be achieved either through a covalent cross-linker or non-covalent cross-linker. Typical the covalent cross-linker of the present invention includes, for example, homobifunctional cross-linkers with reactive molecules of diglycidyl ethers, substituted and unsubstituted diN-hydroxy succinimides (NHS), diisocyanates, diacids, diesters, diacid chlorides, dimaleimides, diacrylates, and the like. Heterobifunctional cross-linkers can also be utilized. Heterobifunctional cross-linkers usually include molecules that contain different functional groups to accomplish the cross-linking, for example, combining NHS and maleimide, an acid and ester, etc.

Non-covalent cross-linkers, e.g., based on ionic, hydrogen bonding and other intramolecular associations are also contemplated for use in the practice of the invention. The non-covalent cross-linkers of the present invention include chitosan/polyacrylic acid, polyacrylic acid/polyethylene glycol (at low pH), polyacrylic acid copolymers and hydroxyl containing polymers, polymers containing carboxylic acid pendant groups, pluronics (ethylene oxide-propylene oxide-ethylene oxide (EO-PO-EO) triblock copolymers), metal cross-linked polymers, ionomers, and the like. For example, the non-covalent cross-linkers of the present invention can be based on hydrophobic associations. Such non-covalent cross-linkers can be any suitable system that demonstrates lower critical association temperatures including, without any limitation, pluronics (triblock copolymers of ethylene oxide and propylene oxide structured as EO-PO-EO), which can form gels at elevated temperatures such as body temperature and convert to a soluble form at a lower temperature such as room temperature.

In one embodiment, the cross-linker of the present invention contains one or more hydrolysable groups. In another embodiment, the cross-linker of the present invention is susceptible to hydrolysis, e.g., either by chemical means or by biological means such as enzyme catalyzed hydrolysis. In yet another embodiment, the cross-linker of the present invention is a polymer or copolymer of lactic acid, glycolic acid, trimethylene carbonate, caprolactone, or any other hydrolysable esters.

In still another embodiment, the cross-linker of the present invention includes a linker between the cross-linking functionalities that renders the ultimate cross-linked polymer a degradation susceptibility towards an intestinal enzyme, e.g., susceptibility to degradation by an intestinal enzyme. These types of cross-linkers typically include basic sensitive groups or $C_{12}$-$C_{22}$ aliphatic unsaturated hydrocarbon linkers, since an intestinal enzyme such as a lipase recognizes fatty acid type structures. In some embodiments, these linkers include diacids that form alpha-omega ester linkages between polymer chains, thereby cross-linking the polymer chains. In addition, oligoesters having alternating PEG spacers can be utilized. Indeed, PEG chains or other hydrophilic spacers can be incorporated into the cross-linkers of the present invention to control hydrophilicity and swelling of the polymers provided by the present invention.

According to another embodiment of the present invention, the polymer used in the present invention can be any polymer that degrades faster in an environment with an intestinal pH, e.g., pH 8. In one embodiment, the polymer of the present invention can be cross-linked hydrogel formulations that are held together by physical cross-links between acid groups and ether oxygens. Examples of acid containing polymers include carboxymethylcellulose, agarose, polyacrylic acid and copolymers, etc. Polymers containing ether oxygens include, for example, any PEGs (branched or linear), any PEG copolymers including, without any limitation, pluronics, polysaccharides, starches, etc.

In another embodiment, the polymer of the present invention includes any polymer containing pendant acid groups or chemically hydrolysable groups. For example, polymers containing one or more pendant acid groups, e.g., carboxymethylcellulose, agarose, polyacrylic acid and copolymers etc, and/or chemically hydrolysable groups, e.g., anhydrides, ketals, acetals, and esters can be covalently cross-linked. In general, as the pH increases in an environment the hydrolyzability of the ester groups in these polymers can increase due to their increased accessibility caused by the polymeric swelling.

Figure 1:
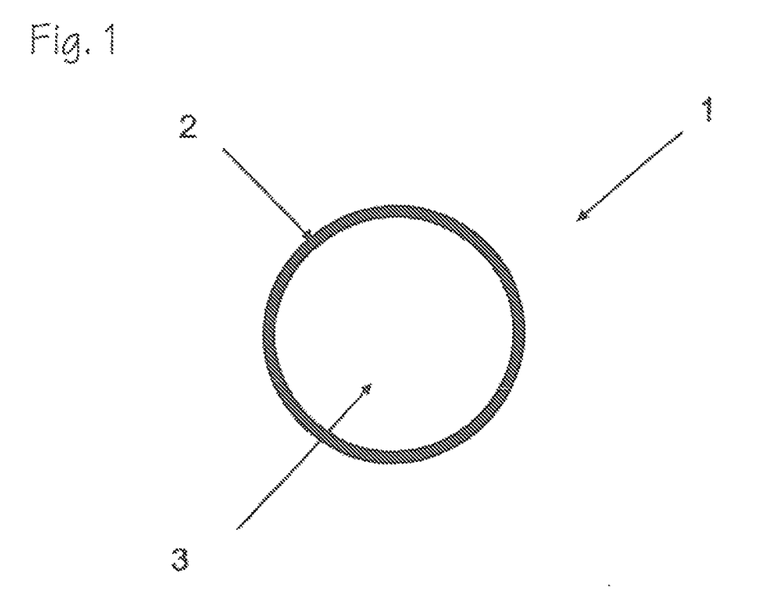
FIG. 1 shows a cross-sectional view of an oral dosage form in tablet form.
Figure 2A:
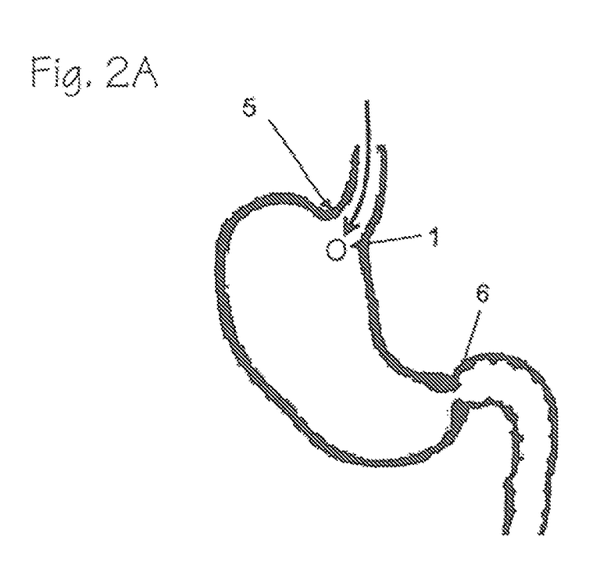
FIG. 2A-2B shows cross-sectional views of the stomach illustrating the ingestion of the polymeric formulation of the invention and its subsequent expansion in the stomach.
Figure 2B:
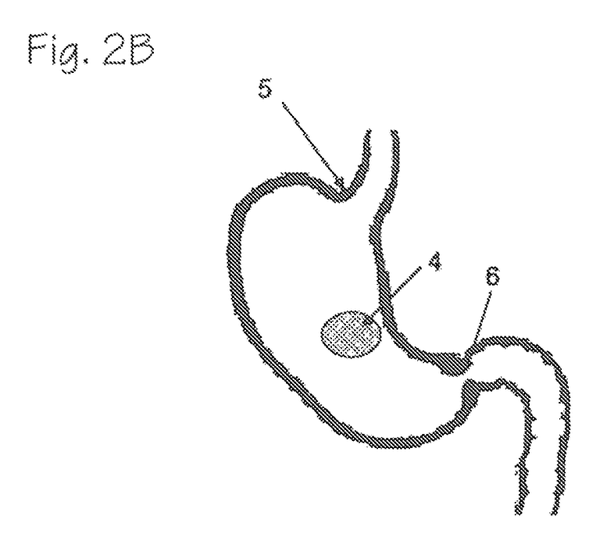

With specific reference now to the figures, FIG. 1 shows a cross-sectional view of an oral dosage form of the invention in tablet form. Specifically, FIG. 1 shows the ingestible compound 1 including a dissolvable coating 2 surrounding the desiccated polymeric formulation 3. In FIGS. 2A and 2B, the tablet is shown functioning in the stomach. In FIG. 2A, the ingestible tablet 1 of FIG. 1 is shown passing the lower esophageal sphincter 5 into the stomach. In FIG. 2B, the tablet 1 is shown after its coating 2 has dissolved and the tablet 1 has expanded to its hydrated form 4. The expanded polymer 4 cannot pass either the lower esophageal sphincter 5 or the pyloric sphincter 6 resulting in its retention in the stomach.

Figure 3A:
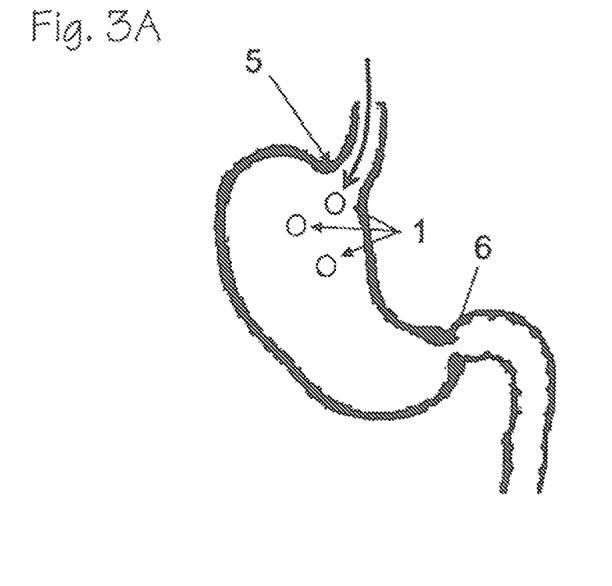
FIG. 3A-3B shows cross-sectional views of the stomach illustrating, the ingestion of multiple tablets of the polymeric formulation of the invention and subsequent expansion in the stomach.)
Figure 3B:
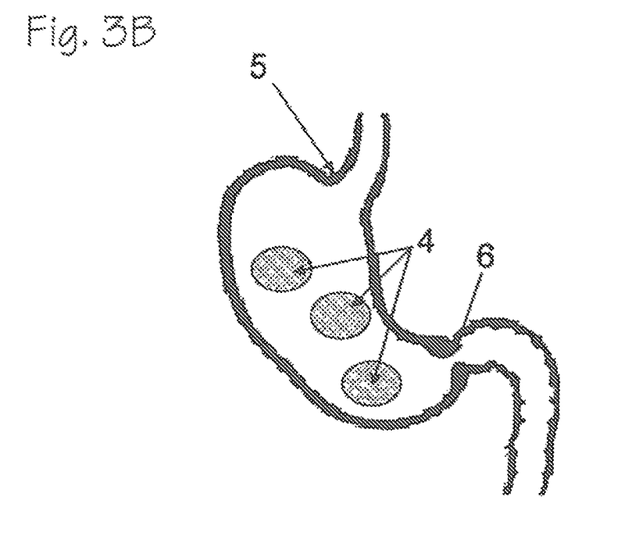

In FIG. 3A-B, multiple tablets are shown functioning in the stomach. In FIG. 3A, the ingestible tablets 1 of FIG. 1 are shown passing the lower esophageal sphincter 5 into the stomach. In FIG. 3B, the tablets 1 are shown after their coatings 2 have dissolved and the tablets 1 have expanded to their hydrated forms 4. The expanded polymers 4 cannot pass either the lower esophageal sphincter 5 or the pyloric sphincter 6 resulting in its retention in the stomach. Obese patients can take as many tablets 1 as are required to produce a sensation of fullness.

Figure 4A:
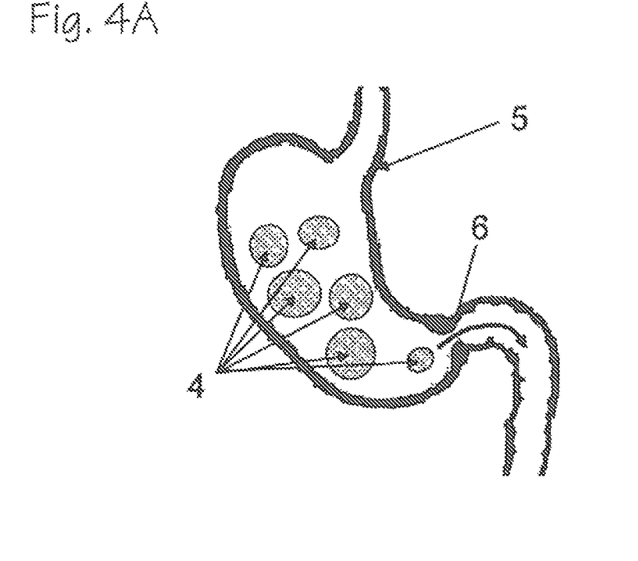
FIG. 4A-4B shows cross-sectional views of the stomach illustrating the presence of multiple tablets polymeric formulations of the invention in various stages of degradation with one tablet sufficiently degraded to pass the pyloric valve and be rapidly degraded in the small intestine milieu.
Figure 4B:
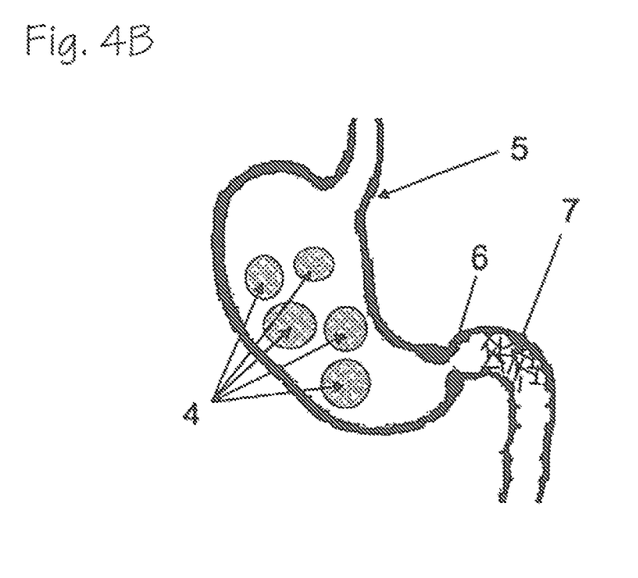

In FIG. 4A, multiple polymeric masses 4 are shown in the stomach in various stages of degradation. One of the masses 10 has degraded sufficiently to pass the pyloric sphincter 6. In FIG. 4B, the polymeric masses 4 are shown in the stomach again with the smallest mass being rapidly degraded in the small intestine to its polymeric precursors 7 after passing the pyloric sphincter 6.

Figure 5A:
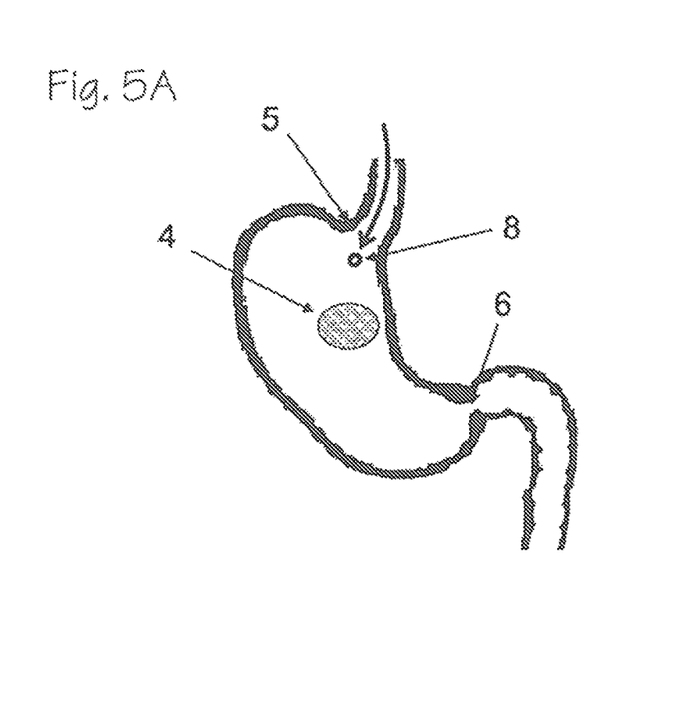
FIG. 5A-5B shows cross-sectional views of the stomach illustrating the presence of a hydrated polymer and the ingestion of a depolymerizer.
Figure 5B:
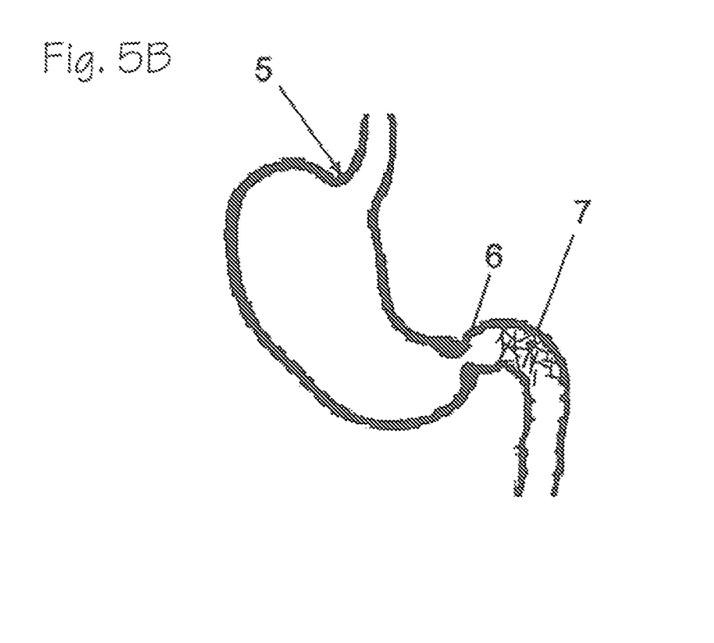

In FIG. 5A-B, the polymer is shown being de-polymerized after its placement in the stomach. In FIG. 5A, the hydrated polymer 4, which cannot pass either the lower esophageal sphincter 5 or the pyloric sphincter 6, is shown in the stomach as de-polymerizer 8 is introduced. The de-polymerizer 8 is shown in tablet form, but may also be in liquid form. In FIG. 5B the de-polymerizer has acted on the polymer 4 resulting in de-polymerization to the polymeric precursors 7. In the case of the alginates and other pH-sensitive groups, the de-polymerizer 8 is a compound which simply raise the pH. In the case of lipid-modified polymers (e.g., acrylates, alginates, cellulose, and the like), the de-polymerizer 8 is a commercially available pharmaceutical grade lipase.

The oral dosage forms and polymeric formulations described herein typically achieve 90% of equilibrium swelling in about 6-18 hours, and typically have completely disappeared from the gut in about 3-10 days. The dosage forms and formulations typically contain an enteric coating so that expansion occurs only in the stomach, and not in the esophagus. Invention oral dosage forms and polymeric formulations typically exhibit swelling resulting in a size increase of about 200%-1000%.

The present invention allows for the safe, controlled distension of the stomach in a noninvasive and completely reversible manner. The oral dosage forms described herein usually include an enterically coated polymeric formulation that is small enough to be swallowed in its pre-gastric state. Once the polymeric formulation reaches the stomach, the coating is dissolved by gastric secretions and the polymer is hydrated resulting, in significant swelling, enough so that the resulting hydrated polymer cannot pass the pyloric valve and remains in the stomach.

The oral dosage forms are designed such that the obese patient can simply continue to ingest additional dosage forms until a sensation of fullness is achieved. The polymer then degrades over time and/or is de-polymerized by ingestion of a specific substance, e.g., a de-polymerizer including, without any limitation, an agent that is capable of raising the pH in the stomach or an intestinal enzyme or derivatives thereof.

Examples of intestinal enzymes include amylase, which hydrolyzes starch into a mixture of maltose and glucose; lipase, which hydrolyzes ingested fats into a mixture of fatty acids and monoglycerides (and its action maybe enhanced by the detergent effect of bile); trypsin, which cleaves peptide bonds on the C-terminal side of arginines and lysines; chymotrypsin, which cuts on the C-terminal side of tyrosine, phenylalanine, and tryptophan residues (the same bonds as pepsin, whose action ceases when the NaHCO$_3$ raises the pH of the intestinal contents); elastase, which cuts peptide bonds next to small, uncharged side chains such as those of alanine and serine; carboxypeptidase, which removes, one by one, the amino acids at the C-terminal of peptides; nucleases, which hydrolyze ingested nucleic acids (RNA and DNA) into their component nucleotides; aminopeptidases, which attack the amino terminal (N-terminal) of peptides producing amino acids; disaccharidases, which convert disaccharides into their monosaccharide subunits; maltase which hydrolyzes maltose into glucose, sucrase, which hydrolyzes sucrose (common table sugar into glucose and fructose; and lactase which hydrolyzes lactose (milk sugar) into glucose and galactose.

The invention is desirable since the oral dosage forms are not metabolically active and do not contain significant calories. Indeed, once the polymer has been de-polymerized and/or degraded, it simply passes through the gastrointestinal tract and is excreted.

A further advantage provided by the invention is the temporary nature of the gastric volume reduction. With current treatments that result in reduction of gastric volume, including gastric bypass, gastric reduction, and intragastric balloons, a significant difficulty exists: adaptation of the stomach to its distended state. By allowing the stomach volume to be temporarily reduced and then returned to its original volume before being reduced again, the present invention reduces the occurrence of stomach distension.

In addition to use in weight loss, the oral dosage forms and polymeric formulations described herein are useful as safe, effective drug delivery systems. The dosage forms and formulations described herein allow for a longer residence time of a drug in the stomach without the risk of small bowel obstruction. Drugs that are taken orally on an hourly basis could instead be ingested on a daily basis using the oral dosage forms and polymeric formulations described herein. The inner core of the oral dosage forms and polymeric formulations described herein would not contain any drug as this would cause a large bolus of drug release with passage and rapid dissolution into the intestine, but the outer layers can be infused with the drug as they must be dissolved prior to any intestinal passage.

In one embodiment, the polymeric formulation provided by the present invention is useful for delivering drugs that, as a solid, are initiating to the gastrointestinal tract such as the mucosal surface or efficacious when administered in a sustained manner. For example, various antibiotics, especially antibiotics useful for eradicating *Helicobacter pylori* from the submucosal tissue of the gastrointestinal tract can be delivered by the polymeric formulations of the present invention.

The invention provides methods for reducing gastric volume in a subject in need thereof. The methods include administering to the subject an effective amount of the oral dosage forms described herein. The dosage forms can be administered orally in the form of tablets, capsules, solutions, emulsions or suspensions. The compositions may be prepared in conventional forms, for example, capsules, tablets. Pharmaceutical formulations containing compounds of this invention can be prepared by conventional techniques, e.g., as described in Remington's Pharmaceutical Sciences, 1985.

In one embodiment, the polymers of the present invention is formed into a packed mass for ingestion, e.g., encapsulated as a "hard-filled capsule" or a "soft-filled capsule" using any suitable encapsulating procedures and materials. The encapsulating material should be highly soluble so that the polymer particles can be rapidly dispersed in the stomach after the capsule is ingested. In another embodiment, the polymer of the present invention is formulated with a soluble binder and compressed into a tablet or pill.

The pharmaceutical carrier or diluent employed may be a conventional solid or liquid carrier. Examples of solid carriers are lactose, sucrose, talc, gelatin, agar, pectin, acacia, magnesium stearate, stearic acid, or lower alkyl ethers of cellulose. Examples of liquid carriers are syrup, peanut oil, olive oil, phospholipids, fatty acids, fatty acid amines, polyoxyethylene or water. The carrier or diluent may include any sustained release material known in the art, such as glyceryl monostearate or distearate, alone or mixed with a wax.

If a solid carrier is used for oral administration, the preparation may be tabletted or placed in a hard gelatin capsule in powder or pellet form. The amount of solid carrier will vary widely, but will usually be from about 25 mg to about 1 gm. If a liquid carrier is used, the preparation may be in the form of a syrup, emulsion, soft gelatin capsule, or sterile injectable liquid such as an aqueous or non-aqueous liquid suspension or solution.

Tablets are prepared by mixing the active ingredient with pharmaceutically inert, inorganic or organic carrier, diluents, and/or excipients. Examples of such excipients which can be used for tablets are lactose, maize starch or derivatives thereof, talc, stearic acid or salts thereof. Examples of suitable excipients for gelatin capsules are vegetable oils, waxes, fats, semisolid, and liquid polyols.

The pharmaceutical products can additionally contain any of a variety of added components, such as for example, preservatives, solubilizers, stabilizers, wetting agents, emulsifiers, sweeteners, colorants, flavorings, butlers, coating agents, antioxidants, diluents, and the like.

Although the invention has been described with reference to the above examples, it will be understood that modifications and variations are encompassed within the spirit and scope of the invention. Accordingly, the invention is limited only by the following claims.

We claim:

1. A method of creating a sensation of fullness in a stomach of a patient, comprising:
   ingesting one or more ingestible tablets formed in a packed mass into the stomach, the ingestible tablets comprising a biocompatible polymer in combination with a solubilizer/stabilization propylene glycol alginate agent which is adapted to maintain the polymer as a firm solid, wherein the polymer further includes one or more lipase-sensitive, fatty acid-like polymerizable groups or cross-linking groups;
   increasing a size of the polymer by absorbing water from gastric fluid such that the polymer is maintained within the stomach for at least 2 hours and a sensation of fullness is induced in the patient without releasing a drug which induces the sensation;
   disintegrating an acid-sensitive gelatin coating such that the polymer disintegrates in the gastric fluid and disperses in the stomach at a first degradation rate; and
   further disintegrating the polymer within an intestinal tract of the patient upon exposure to an intestinal enzyme or an intestinal pH at a second degradation rate which is higher than the first degradation rate, wherein the second degradation rate is sufficiently rapid to substantially prevent a small bowel obstruction by the polymer.

2. The method of claim 1 wherein the polymer is selected from the group consisting of polyvinyl alcohol, poly(ethyloxazoline), polyvinylacetate-polyvinylalcohol copolymers, poly(2-hydroxyethylacrylate-), poly(2-hydroxyethylmethacrylate, polyacrylic acid, and copolymers thereof, polysaccharides, water soluble proteins, and polynucleic acids.

\* \* \* \* \*

UNITED STATES PATENT AND TRADEMARK OFFICE
CERTIFICATE OF CORRECTION

PATENT NO. : 9,782,348 B2  
APPLICATION NO. : 15/213285  
DATED : October 10, 2017  
INVENTOR(S) : Daniel R. Burnett et al.

Page 1 of 1

It is certified that error appears in the above-identified patent and that said Letters Patent is hereby corrected as shown below:

In the Claims

In Claim 2, Lines 4-5, please replace "poly(2-hydroxyethylmethacrylate" with --poly(2-hydroxyethylmethacrylate)--.

Signed and Sealed this  
Twenty-ninth Day of May, 2018

Andrei Iancu  
*Director of the United States Patent and Trademark Office*